(12) United States Patent
Olivares Godoy et al.

(10) Patent No.: US 8,752,423 B2
(45) Date of Patent: Jun. 17, 2014

(54) METHOD FOR INSPECTING TIRES, ENABLING THE ON-SITE DETECTOR OF DEFECTS, THE STATE OF WEAR OF THE RUBBER, OR THE INTERNAL CONDITION OF THE TIRE

(75) Inventors: Marcelo Alberto Olivares Godoy, Antofagasta (CL); Enrique Arnoldo Olivares Miranda, Antofagasta (CL)

(73) Assignee: Universidad Catolica del Norte, Antofagasta (CL)

( * ) Notice: Subject to any disclaimer, the term of this patent is extended or adjusted under 35 U.S.C. 154(b) by 122 days.

(21) Appl. No.: 13/377,442

(22) PCT Filed: Jun. 10, 2010

(86) PCT No.: PCT/CL2010/000020
§ 371 (c)(1),
(2), (4) Date: Jan. 19, 2012

(87) PCT Pub. No.: WO2010/142054
PCT Pub. Date: Dec. 16, 2010

(65) Prior Publication Data
US 2012/0131995 A1 May 31, 2012

(30) Foreign Application Priority Data
Jun. 10, 2009 (CL) .................................. 1393-2009

(51) Int. Cl.
*G01M 17/02* (2006.01)
*B60C 23/02* (2006.01)

(52) U.S. Cl.
USPC .......................................... 73/146; 73/146.5

(58) Field of Classification Search
None
See application file for complete search history.

(56) References Cited

U.S. PATENT DOCUMENTS

| | | | | |
|---|---|---|---|---|
| 3,978,712 A | * | 9/1976 | Cowan et al. | 73/598 |
| 4,275,589 A | * | 6/1981 | Dugger et al. | 73/146 |
| 4,285,235 A | * | 8/1981 | Dugger | 73/146 |
| 4,297,876 A | * | 11/1981 | Weiss | 73/146 |
| 4,327,579 A | * | 5/1982 | Weiss | 73/146 |
| 4,337,660 A | * | 7/1982 | Weiss | 73/600 |
| 6,069,966 A | * | 5/2000 | Jones et al. | 382/100 |
| 6,789,416 B1 | * | 9/2004 | Tracy et al. | 73/146 |
| 7,061,381 B2 | * | 6/2006 | Forcier et al. | 340/572.2 |
| 8,009,027 B2 | * | 8/2011 | Thomas et al. | 340/447 |
| 2005/0268707 A1 | * | 12/2005 | Dale et al. | 73/146 |

(Continued)

OTHER PUBLICATIONS

Russell, Emily; Shortage of OTR Tires will last Until 2009-2010—Regional; Business News Americas Latin America's Business Information Leader; Sep. 11, 2006.

(Continued)

*Primary Examiner* — Andre Allen
(74) *Attorney, Agent, or Firm* — Colin P. Cahoon; Celina M. Orr; Carstens & Cahoon, LLP

(57) ABSTRACT

The invention relates to a technical inspection method which comprises the specific application of an ultrasound wave perfectly adapted for interacting with the rubber and for detecting: defects, tears, gaps, the state of wear of the rubber, and the breakage of steel wires or meshes in giant OTR (off-the-road) tires. Said inspection consists of injecting, into any sector of the tire and using an ultrasound defect detector device, ultrasound waves that generate echoes by bouncing off breaks or interfaces in the material, the assessment of which yields a diagnosis of the internal condition and operating state of the tire.

19 Claims, 1 Drawing Sheet

(56) References Cited

U.S. PATENT DOCUMENTS

| | | | |
|---|---|---|---|
| 2006/0181421 A1* | 8/2006 | Forcier et al. | 340/572.1 |
| 2007/0279203 A1* | 12/2007 | Thomas et al. | 340/447 |
| 2008/0216567 A1* | 9/2008 | Breed | 73/146.5 |
| 2012/0008148 A1* | 1/2012 | Pryce et al. | 356/601 |

OTHER PUBLICATIONS

Brundell, Robin; Offer of OTR Tires Would Not Recover until the End of 2010—Regional; Business News Americas Latin America's Business Information Leader; Jan. 23, 2007.

* cited by examiner

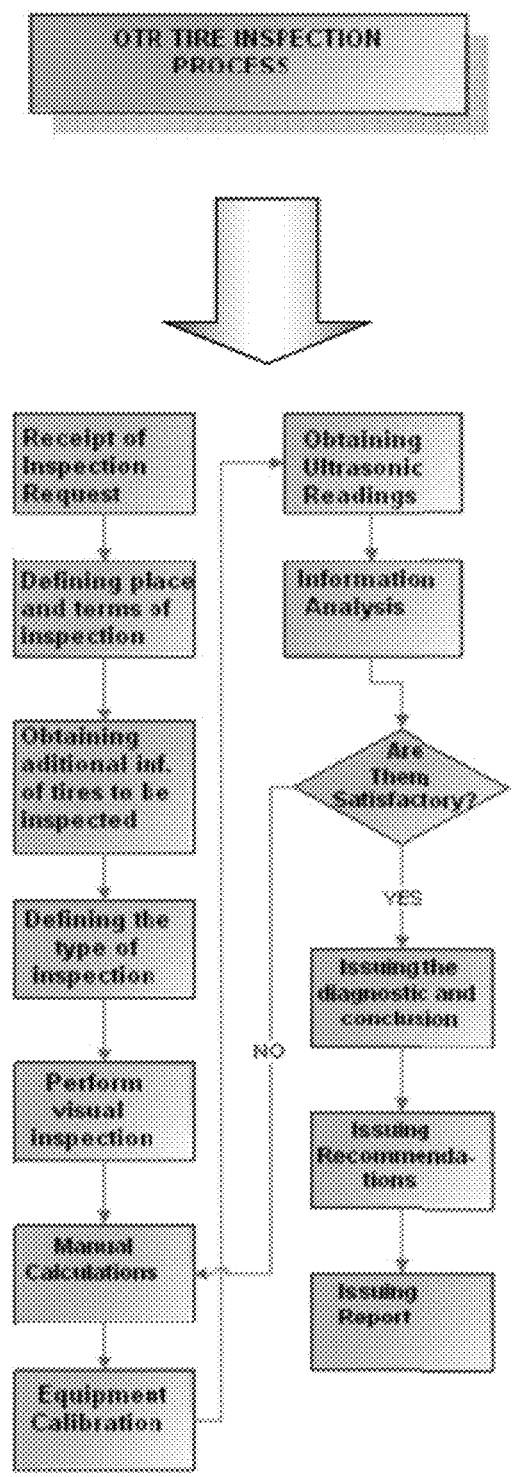

METHOD FOR INSPECTING TIRES, ENABLING THE ON-SITE DETECTOR OF DEFECTS, THE STATE OF WEAR OF THE RUBBER, OR THE INTERNAL CONDITION OF THE TIRE

FIELD OF THE INVENTION

The present invention relates to a method comprising the specific application of a perfectly built up and conditioned ultrasonic wave, which can interact with rubber and—by means of a specific technique, detect defects, heterogeneities, and lack of continuity in large size giant tires called OTR (Off the Road Tires), used in every mining site worldwide. Special reference is made to heavy-duty trucks used for ore transport, front-end loaders, land movement equipment, pailoaders, tractors, etc., and, in general, to every mining site machinery with tire rims ranging from 22 to 70 inches. Such technique allows verifying, assessing, and determining tire internal damages as well as rubber degradation states by using more refined ultrasonic waves in their non rectified radiofrequency-type and square wave-type modes.

BACKGROUND OF THE INVENTION

With regard to its physical characteristics, rubber as the main component used to manufacture tires, is structurally composed of long linear polymer chains. Their main components are: "natural rubber" which is form from poly (cis-isoprene) and "synthetic rubber" which is normally obtained from a polymerization of styrene and butadiene.

The exact proportions and the addition of other elements in the manufacture of every type of tire are regarded as confidential information closely kept by manufacturers.

These linear polymer chains are cross linked through a process called vulcanization in order to prevent the individual chains from sliding past each other and also to transform these linear chains into a three-dimensional network, linking chains with each other via knots. The resulting product is known as "elastomer".

With regard to elastic behavior versus rubber temperature, in the absence of disturbances, the elastomer chains form what is called the statistical coil, but if an external force is applied, the sample is able to increase its size without modifying either valence angles or bond lengths, but simply by passing to a larger shape. That is, rubber is composed of long molecules capable of stretching or compressing when an external force is applied; when this external force disappears, the chain recovers the equilibrium distribution, so the process is reversible.

Entropy is the fundamental magnitude in the stretching process: when chains are stretched their entropy decreases; so when the stretching force is removed, chains return to the initial state increasing the entropy. This is based on the theory of rubber elasticity.

With regard to the incidence of another state of excitation, the behavior of rubber and temperature can be easily studied. In a simple experiment, one end of a piece of rubber is fixed to a wall by a nail and from the opposite end an object for keeping the rubber stretched is attached; marking somehow the position of the rubber end. If we now heat the rubber with hot air, it will be verified that instead of stretching, the rubber shortens, contrary to what happens with metals which expand under heat. This is the result of the following process: when the material is heated, its molecules move more energetically as the temperature rises.

There are several causes of tire failures, the most common ones are: overloading, over pressure, inadequate roads, excessive temperature, fatigue of material, poor handling, etc., some of them are inevitable since they occur in highly productive mining sites; however, they are not exempted from minimizing tire damages. The goal is to extend the lifespan of every tire by maximizing the unit yield thereof.

Upon considering the process where a failure is generated by causes such as overloading or TKPH (Ton-Kilometer per Hour), there will always be a period of damage incubation or minimum state of evolution, and during this starting state, it is the best time to detect a discontinuity in the form of cracks or micro-cracks.

The basic concept of fracture mechanics indicates that when the mechanical strength limits of all materials used in engineering are exceeded, they show their "ailments" or status of "discomfort" in service via symptoms of fatigue, which modify their mechanical characteristics or states of operative agitation resulting in increased temperature of service which eventually causes collapse or catastrophic failure. On the other hand, from the point of view of failure analysis, the final breaking is an evident result of the material relaxing state and stress relief. The design engineering always takes into consideration and expects that materials are subjected to stress and mechanical stress within the creep limits (elastic deformation), but they are expected not to exceed their maximum stress values, so that, in the first place, their mechanical characteristics will not be altered and on the second place, they will not break. In the end, material degradation always builds up a group of symptoms which are associated with the presence of failure.

Currently, in every ore extraction process, tires have become an expensive element of sacrifice. Tires are subjected to high stresses and severe mechanical stress; due to their design, neuralgic zones or stress concentrating points capable of causing failures are generated therein. When the loaded truck passes over curves, tires are subjected to stress, complex models of dynamic stresses with components of high stress values are formed therein, which are obviously not considered in the design, being these components more severe and dangerous when their operative, inflation pressure and load parameters are exceeded and do not meet the specifications.

On the other hand, ultrasounds are acoustic waves which are identical in nature to sound waves, which differ from the latter in that their frequency is well above the audible zone. Within the acoustic spectrum, the three following bands can be distinguished:

a. Infrasonic: Frequencies below 16 cycles/second Hertz (Hz).
b. Sonic (audible): Frequencies ranking between 16 Hz and 20 (Khz.)
c. Ultrasonic: Frequencies above 20 kHz. The limit of the frequency is not physically defined and, in practice, it depends on the possibility of its generation and reception.

As the origin of the methods of Non-Destructive Testing (NDT) to identify tire failures/defects the well known percussion test can be considered wherein the sample is hit by a hammer and the sound is perceived by the ear.

However, first nondestructive testing via ultrasounds applied to materials other than rubber itself, were applied by Sokolov, in 1929, to detect the presence of heterogeneities by measuring the drop of the acoustic intensity transmitted through the material when a ultrasound beam goes through the analyzed object which comprises heterogeneities or defects: today it is the "transparency method". Later, in 1942, Firestone applied the principle of the "sonar" which was used for the localization of vessels and carrying out measurements in the deep sea. This approach was used for the detection of material heterogeneities through a reflected signal, which is currently known as "pulse-echo method".

Ultrasonic waves propagate by taking advantage of the elastic properties of the bodies and thus, they require the existence of a material medium (atoms and molecules), that is, unlike the electromagnetic wave, these waves can not propagate in vacuum.

Ultrasonic energy propagation through a given medium occurs thanks to the vibration of the constituent particles and to the interaction derived from the cohesive forces thereof. Thus, every propagation medium constituent particle behaves as an oscillator that vibrates subjected to forces derived from a disturbance from its equilibrium position with regard to its neighbors. The progress or propagation of this disturbance is known as "wave", whereas waves in elastic media could be called mechanical waves. Mechanical waves are characterized by the propagation of energy through matter by means of regular and constant motion of a disturbance which progresses through matter, without moving the matter itself. Ultrasonic waves have been divided into several types according to their form and way of propagation.

Longitudinal waves are those where the particles of the transmission medium move in the same propagation direction, whereas transverse waves are those where particles vibrate at right angle to the direction of the wave. An isotropic solid is capable of propagating both types of waves, thus in an ultrasonic inspection both longitudinal and transverse waves are used. Under appropriate conditions, it is possible to transmit ultrasonic vibrations with considerable amplitude through surface waves, where the particle motion describes an elliptical path in the plane formed by the propagation direction and one perpendicular to surface, the minor axle being parallel to the propagation direction. The mechanics of this type of waves is very similar to that of waves that propagates over a free surface of a liquid. They are known as Rayleigh waves.

The propagation speed of longitudinal, transverse, and surface waves, in a given medium, depends on the nature thereof. More precisely, it is a function of its Young's modulus, its density, and its Poisson's modulus.

The ultrasound property of propagating in the form of beams with little divergence is fundamentally important in the ability of this method to locate and dimension material internal defects. From the application point of view, another interesting physical phenomenon associated with ultrasounds is the attenuation. This phenomenon, which relates to the loss of wave amplitude during its propagation through a certain material, would be caused by four different mechanisms: dispersion, internal friction, elastic hysteresis and thermal dissipation.

Dispersion losses occur when the wave travels through small discontinuities or heterogeneities which mean, for example, grains and grain boundaries which are typical of metallographic structures of the majority of engineering materials. In each of these ones, a part of the energy is dispersed in the form of waves which either reflected or refracted deviate from the main beam.

On the other hand, upon vibration caused by the travel of an ultrasonic wave, among the same grains a viscous friction is produced which dissipates, in the form of heat, part of the energy thereof.

Generally, solids do not have a perfect elastic behavior and any mechanical disturbances produce displacements and changes in the arrangement of atoms and molecules of materials. In turn, these phenomena absorb energy from the ultrasonic beam, thus reducing the amplitude of their oscillations. Finally, an ultrasonic wave which propagates through the material, causes the material to interchangeably pass from compression states to expansion states, resulting in heating and cooling, though not perfectly adiabatic.

When an ultrasonic pulse influences the interface between its propagation medium and another medium of different nature, part of the energy thereof travels to the second medium in the form of a transmitted wave and a part thereof remains within the first medium in the form of a reflected wave. Consequently, the amount of energy reflected by an interface between two given media depends on the acoustic dissimilarity between each other.

From the point of view of material testing applications, ultrasound (US) wave main characteristics are the following parameters:

Frequency (f; 1/T; [Mhz])

It is the number of oscillations experimented by a given particle per every second. Frequency, within the same wave, is the same for every particle and is equal to the generator frequency, which can be arbitrarily chosen.

Wavelength

It is the distance between two planes wherein particles are in the same state of motion. It is inversely proportional to frequency.

Wavelength ($\lambda$; L; [mm])

Acoustic Speed (v; L/T; [Km./s])

It is the wave propagation speed for a given condition, for example, a compression zone. This speed is characteristic of the material and is generally constant for a given material, for any frequency and any wavelength. Among acoustic speed, frequency and wavelength there are the following relationships:

$$\lambda = v/f$$

Acoustic Impedance (Z; M/L$^2$T; [Kg./m$^2$s]

Acoustic impedance is a resistance that opposes the wave vibration. If a medium possesses low impedance, it will offer low resistance to elastic deformations caused by waves; whereas, on the other hand, if the impedance is high, the medium will offer high resistance to elastic deformations. Therefore, impedance opposes to mass element vibration but it does not oppose to wave propagation. The acoustic impedance is defined as follows:

$$Z = v \cdot \rho$$

Wherein $\rho$ corresponds to density and "v" to the material acoustic speed. It can be observed that the acoustic impedance is a material constant.

Acoustic Pressure (P; M/LT$^2$; [Pa])

In zones of material compression, pressure is higher than normal pressure, whereas in dilated or expanded zones, pressure is lower. This alternating pressure is the acoustic pressure and occurs not only in gasses but also in solids and liquids. Maximum deviation with regard to normal pressure, that is, without acoustic waves is called acoustic pressure amplitude and it is closely linked to oscillation amplitude. In the case of plane and spherical waves, acoustic pressure and oscillation maximum amplitude are related by:

$$Z = \rho v = Z \omega w A$$

Expression wherein Z is the acoustic in $\omega$ since and angular f ($\omega = 2\pi f$).

From this formula, it can be deduced that for longitudinal waves, the acoustic pressure as a force per unit of normal surface to wave surface, and for transverse waves, the shear force per unit of surface parallel to the wave surface.

Specific Acoustic Energy ($E_e$; $M/LT^2$; [$W/m^3$])

Wave propagation is characterized by energy transport and not by mass transport. Energy present in the medium volume unit (which progresses with acoustic speed) is called wave specific energy. In the case of plane and spherical waves, it is expressed as:

$$E_e = \tfrac{1}{2}\rho v^2 = \tfrac{1}{2}\rho \omega A^2 = \tfrac{1}{2}P^2/\omega v^2 = \tfrac{1}{2}P^2/Zv$$

This formula relates amplitude, A and acoustic pressure, P, with the specific acoustic energy Ee.

Acoustic Intensity (I, $M/T^3$; [$w/m^2$])

It is the amount of energy which travels through the unit of area per the unit of time and it is the product of the specific energy and acoustic speed. The following expressions are obtained in the case of plane and spherical waves:

$$I = \tfrac{1}{2}\rho C v^2 = \tfrac{1}{2}Z v^2 = \tfrac{1}{2}Z\omega^2 A^2 \tfrac{1}{2}P^2/Z$$

Amplitude (A, L; [mm])

It is the maximum displacement of a particle from its resting (zero) position. It is measured in mm.

Longitudinal waves are the ones with true audible character. For these waves, the oscillations occur in the direction of the wave propagation. Since the compression and dilatation forces are active in these waves, they are also called pressure waves, and due to the fact that their particle density fluctuates, they have also been called density waves.

They can propagate in every kind of medium: gasses, liquids and solids, and they are regarded as the most simple and used type of wave within ultrasonic technology. In fact, practically every ultrasound transducer or scanner emits longitudinal waves and from those waves the rest of the wave types are generated, either due to the medium geometry or due to the conversion of the vibration mode.

The specific propagation speed depends on the modulus of elasticity, shear modulus, and Poisson's ratio of the propagation material or medium.

In the acoustic wave propagation, "limit surface" is regarded as the one which separates two mediums with different elastic properties. It is evident that if a material is surrounded by an empty space, it can not transmit any kind of acoustic wave and this wave travels back one way or another. If another material is adhered to the first one, the acoustic wave will propagate, more or less altered with regard to direction, intensity and mode.

For studying the behavior of ultrasonic waves in limit surfaces, two cases should be taken into consideration: The beam influencing in a perpendicular or normal way, or in an oblique or angular way.

If an acoustic wave whose wave front is plane reaches the limit surface between two media, with a 90° angle, a part of the wave energy is reflected and travels back to the first medium in the same direction as the incident wave; another part will propagate to the second medium keeping its direction and way.

It should be assumed that wave propagation is characterized by energy transport and not by mass transport.

The law of conservation of energy says: "in nature nothing can be destroyed, everything changes". This implies that when a body or material which is in elastic equilibrium, with all its particles equilibrated by elastic forces, is provided with a certain amount of energy, surface particles will communicate the received energy with their neighbor particles and these particles in turn will do the same with their neighbor particles, thus generating an energy propagation through all particles within the medium.

However, as all bodies normally have a limit surface around them such as air, solid, or liquid, all the energy affecting a body will not be transmitted through it but a certain amount of this energy will be reflected through this limit surface.

Since air and gasses in general strongly attenuate sound transmission, it can be deduced that is advisable to use an acoustic conducting medium located between the scanner and the test sample so that the air gap between them is displaced and thus the incident acoustic pressure is allowed to enter the sample to be examined.

Acoustic Coupling Mediums are rather viscous liquids. Generally, they are pasty organic compounds which should have the following characteristics:

Should wet the surface of the material to be examined as well as the scanner in order to remove the air gap between them.

Easy to apply.

Should not spread out too fast on the surface

Should be homogeneous and bubble free, or solid particles capable of reflecting or deviating US beam.

Non-corrosive and non-toxic.

Should have an intermediate acoustic impedance between the test sample and the transducer.

The widely used coupling media are the following:

Water: Moisturizing, degasifying and antioxidant agents should be added to water. Water is mainly used in immersion techniques.

Light oil: It is the coupling medium most extensively used in the contact technique. It remains on the surface for a long time. Oils with moisturizing additives should be preferred.

Glycerin: It is an excellent coupling medium due to its appropriate acoustic impedance as well as its good surface adherence. Generally, this medium is not used in its pure form but with two parts of water and a small amount of a moisturizing agent.

Glycerin is the coupling medium used in the OTR tire inspection.

When we speak of sound field, this is regarded as unlimited from its definition point of view. Every point in space can be made to match the pressure amplitude in space, which in certain cases could be null. The group of these points and their acoustic pressure values comprise the sound field which should be called variable acoustic pressure field.

The way acoustic pressures are distributed in space is a characteristic of every sound source. However, strictly speaking, the tool through which heterogeneities are detected in a material is not a scanner itself but the acoustic field generated by this tool.

In an ideal material, acoustic pressure is only attenuated by virtue of the wave divergence. Accordingly, in a plane wave the acoustic pressure is not attenuated during its propagation, and in a spherical wave, or in the ultrasonic beam far field of a scanner, the acoustic pressure decreased inversely proportional to the distance from the source.

However, solid materials cause a rather strong attenuation effect which results in ultrasound weakening, this phenomenon relates to the loss of wave amplitude during its propagation due to two causes: dispersion and absorption, both being constituent parts of the attenuation (also called damping or extinction).

Losses due to dispersion result from materials whose structures are not perfectly homogeneous. They contain small limit surfaces or interfaces, where acoustic impedance changes drastically due to the material different density and acoustic speed, its nature, condition, or different states among such interfaces. In the nature of metallic materials, these small heterogeneities can be inclusions (non-metallic), pores, graphite precipitates as in the case of grey cast, whose elastic properties are very different from those of ferrite, phases with different compositions in the crystal structure, etc. In each of these discontinuities, one part of the energy is dispersed in the form of waves which, reflected or refracted, deviate from the main beam.

On the other hand, when the grains vibrate after an ultrasonic wave passes through, a viscous friction occurs among them. This viscous friction dissipates part of the initial energy of the ultrasonic wave in the form of heat. This phenomenon is known as absorption; thus we can say that absorption is a direct conversion of ultrasonic energy into heat due to several processes. Absorption can be explained in an elementary way as a braking effect of the particle oscillation which would explain as well why a fast oscillation loses more energy than a slow energy. Absorption increases generally with frequency but to a lower extent than dispersion.

BACKGROUND OF THE INVENTION

Traditionally, a way of recognizing the existence of a possible defect in a tire is by carrying out the so-called "percussion test" which consists in banging with your fist, a hammer or another blunt element the area in question and capture with the naked ear "differences" in the clarity of the sound perceived between two adjacent areas; if this occurs, it is a sign that some disturbance exists. Subsequently, to verify the presence and the extent of the alleged and sometimes inexistent defect, repair workers dig under the area with a reamer and tear the material until verifying through ripping the extent of the damage. Once this is carried out, typically the final digging dimension exceeds the manufacturer's recommended limits for carrying out repairs. Consequently, such a ripped tire is discharged and its remaining rubber is wasted.

In this scenario, every action taken towards introducing in this field new highly technified work practices that efficiently increase the unit performance and reliability is unquestionable and beneficial.

By virtue of the previous explanations, the present invention solves this problem of the art by letting radiofrequency ultrasonic waves or square waves in which interact with the rubber of the OTR giant tires and through their echoes they provide us with defect, degradation state and internal condition data.

Documents WO2004019028A2, JP7103949A and WO1990002946A can be considered similar to the proposed invention with regard to the state of the art.

Document WO2004019028A2 protects a portable apparatus intended for inspection through ultrasound, particularly adapted to examine a container. The apparatus sends an ultrasound pulse to be reflected by the container back wall and obtain data from the echo that was received as an answer and thus determine certain information about the container contents.

The invention mentions a gun-shaped ultrasound apparatus ("Ultrasonic Gun") that uses two 200 Khz and 1 Mzh frequency transducers designed to identify substances or materials inside a hermetic receptacle or sealed container. Due to the range of frequencies, the apparatus has a very limited, very specific application with reduced versatility. Therefore it can not be used in a tire inspection since rubber is a material with low transparency to ultrasound. Consequently, this instrument technology is insufficient.

This is an ultrasonic inspection apparatus particularly adapted to examine the contents of hermetic receptacles that can not be opened and other dubious origin receptacles. Such contents can be liquid, solid or semi-solid material. The apparatus has the shape of a gun that is held and operated manually. At its end or front end there is one low frequency transducer and one high frequency transducer plus a temperature sensor. This part of the apparatus is the one that is placed in contact with the surface of the container wall to be inspected. A basic technology ultrasound pulse comes out of the gun and enters the container and travels or is transmitted through the wall and liquid or material inside the container. During its passing this initial ultrasonic pulse suffers transformations or modifications either due to the temperature, type of material of the container, time and distance traveled, which in the end will have to do with the container or receptacle dimensions and physical features of the contents. These transformations will be reflected in the back "echo" or modified return signal that arrives at the instrument which in turn, via an electronic processor, delivers the return signal in the form of a specific digitalized wave that should be interpreted by the operator. Obviously, the operator has carried out previous calibrations, entered data for measurements, adjusted parameters, etc.

The great majority of the materials used in engineering are transparent to ultrasound; however, some materials as the "rubber" are more difficult to cross.

Lets remember that ultrasonic waves are acoustic waves identical in nature to sound waves, and the only difference between them is that the ultrasonic wave frequency is high above the audible area: infrasonic, frequencies lower than 16 cycles/sec. (Hz); sonic (audible), frequencies comprised between 16 Hz and 20 (Khz); ultrasonic (non-audible), frequencies higher than 20 (Khz).

Ultrasonic waves make use of elastic properties of a body to propagate, and that is why they require the existence of a material medium (atoms and molecules), i.e., unlike electromagnetic waves they cannot propagate in vacuum.

When an ultrasonic wave reaches a material surface it elastically deforms an atom plane which in turn transmits such deformation to the neighboring atomic planes due to the existent interactions or interatomic cohesion forces. In this way the ultrasonic wave penetrates and travels through a specific body. The energy that is present within an ultrasonic wave creates the oscillatory stress needed to produce the movement of the first plane which is transmitted to the other planes inside the material with a certain speed, typical in each material.

Finally, if a crystal material has practically constant elastic properties, regardless the direction from which a mechanical effect is presented from outside, then we say that this material is "elastically isotropic", and we talk about a reduced "elastic anisotropy" of the material. The materials with reduced elastic anisotropy are often transparent to sound and as a general rule they can be perfectly verified through ultrasounds. In short we can say that a material with an organized and uniform "texture" has good transparency to ultrasounds.

Nevertheless, as it has been already said, in the case of rubber the situation changes radically. Rubber belongs to the polymer family, particularly to those called elastomers, and in no case these materials account for a perfectly adiabatic, homogenous, uniformly organized medium for an ultrasound transmission. Its molecules are elongated and disorganized and when they are excited, they consume high energy which is mainly attenuated through dispersion because they are deformed in many directions due to their amorphous condition. A three-dimensional structure, which also improves its mechanical properties, is achieved only by a vulcanization process.

Given these difficulties, in the field of Non Destructive Testing, there were only weak and unfinished attempts of rubber testing that were carried out by a few equipment manufacturers.

On the other hand, the present invention, as it has been seen previously, do not lie in the design of an ultrasonic wave generator apparatus or instrument but instead it consists in and seeks to protect the fulfillment of the ultrasonic technique development and the applicability of its parameters in order to detect defects in OTR tires, regardless of a particular ultrasonic equipment or instrument that could be used.

Also, the ultrasonic gun uses 200 Khz and 1 Mhz transducers, thus its functionality is limited to these frequencies. The tire vulcanized rubber, depending on some physical and mechanical features, requires a frequency ranging from 0.3 Mhz to 2.5 Mhz for its inspection.

Only in its high frequency circuit the ultrasonic gun uses the square waveform, i.e., up to 1 Mhz, a condition that absolutely rules out the possibility of using this apparatus in a tire inspection.

The present invention considers the use of a wave without rectification, i.e., in the "radiofrequency" mode, which allows us to display important rectification options and wave mode to select the modality that gives us a more accurate and clearer oscillogram through all scanning thickness. In turn, the ultrasonic gun, among other things, does not have such a significant advantage because it is not an equipment intended for versatility, and it is not designed either for special applications in materials that are difficult to penetrate as the rubber.

"The ultrasonic gun" does not have the screen display option in frequencies up to 25 Mhz., which allows us to carry out the "ultrasonic scanning" comprising significant thickness areas on the tire tread. This approach is used in each inspection to improve testing times.

The accuracy of the ultrasonic testing of a tire depends greatly on the changes in the rubber temperature and the most influencing parameter in this testing is the speed of sound which, as it has already been mentioned, is a specific feature. Furthermore, it has been proven that different speeds of sound are given for the same type of tire which is manufactured by different manufactures.

Theoretically, the vulcanized rubber has a 3.6 km/sec. speed of sound; its density is from 1.1 to 1.6 gr/cm3; its acoustic impedance is from 0.25 to 0.37 gr/cm2-sec. The ultrasonic gun works by entering manually, during its initial adjustment, the speed of sound of the material that is allegedly expected to be found inside but without compensating the variations that could occur as those previously mentioned.

The document WO1990002946A protects an ultrasonic quality control station-type apparatus for conventional tire inspection and defect detection. The device makes the tire turn round at a constant rate and has two transducer devices, one transmission device that directs a plurality of consecutive burstings collimated with ultrasonic energy against the tire face and the reception transducer from one side of the tire.

This is a steady apparatus with hydraulic, electrical and mechanical components fixed on the floor by a certain anchoring system. It has the appropriate size for an ultrasound inspection of conventional tires of vehicles or light duty vehicles that do not exceed certain sizes. It has been intended to be installed during the quality control stage of the production line of a mass-production tire plant; to detect possible typical structural damages of the manufacturing processes. Engineering and development put more emphasis on mechanical equipment design than inspection system technology.

It works as follows: the tire to be inspected is placed on an axle activated by an engine. Fixed to an arm placed on the tire tread, 16 ultrasound emission mini-transducers are installed and on the back side of the tire tread, and interior part of the tire, the same number of receiver transducers are placed and carefully distributed in a fan shape. The tire is turned all they way round at 2 to 3 minute constant rate, synchronized with the collimated ultrasonic energy emission and reception of the transducers. If the presence of a defect is detected in the tire, the mechanism provides an automatic ink marking system of the area in question.

It has a control rack where all resulting data from the inspection is digitally displayed in addition to the appropriate data register.

In turn, the present invention is an ultrasound application aiming to in-situ OTR giant tire inspection (diameter: 3.7 meters; weight: around 5.000 kg or higher) since the invention itself is an ultrasound application technique, ultra portable, with the intervention of an ultrasound skilled analyst and a harness-held instrument weighing around 2.6 kg; it does not require any type of installation. It is apparent that the ultrasonic quality control station of the prior art could not be useful for this purpose because the tires to be analyzed are giant and their emerging defects need to be diagnosed at working site.

The nature of the defects that can occur during the manufacturing process of conventional tires of light duty vehicles are not related to the defect generation or damages produced during a giant tire service.

The causes of defect generation in these large size tires are related to complex stress states which end up with rubber severe cracking with a difficult diagnosis: small cracks or separations are originated in these points where the stress is concentrated that sometimes, after little use, they end up triggering large defects whose detection require "state-of-the-art instruments and work technique having the required electronic advantages to carry out more accurate diagnosis." Ultrasound analyst-operator workers should be highly skilled with specific and broad theoretical knowledge of material science and defectology.

A small and non-mobile mechanism as the ultrasonic quality control station mentioned above is useless for giant tire inspection since its limited use is adapted and designed for conventional tires. Furthermore, it works with the mechanized GoNoGo system which requires only one person with minimum skills to be operated.

Finally, document JP7103949 A discloses a high sensitive system for tire defect-detection through an ultrasonic test. It uses method wherein ultrasonic pulses are transmitted from an ultrasonic vibrator and only propagate through an ultrasonic medium and a tire.

FIGURE DESCRIPTION

FIG. 1. shows a flow diagram of the present invention.

DETAIL DESCRIPTION OF THE INVENTION

The present invention relates to the fulfillment of a research process designed for defect detection, defects occurring in large size giant tires known as OTR (Off The Road), to establish the internal condition or degradation state of the rubber by ultrasound technology using radiofrequency-type waves or square-type waves. The process consists of having all these waves perfectly conditioned so that they can be transmitted through the rubber, generating reflections or echo responses originated from discontinuities, in order to provide information about the internal condition thereof.

With regard to FIG. 1, the following phases of defect detection procedure are detailed.

Phase 1. Receipt of Inspection Request:

In this phase the inspection process refers to the reception of an instruction to carry out the inspection by the work team in charge of the service. The instruction can be either an oral instruction or a formal instruction by a document known as service or work order.

Phase 2. Defining inspection place and terms:

This phase of the inspection process consists in setting the precise physical place where the inspection will be carried out. Whether it will be in situ or in a repair shop; post operation or post repairs.

Phase 3. Collecting appropriate information about the tire to be inspected:

This phase of the inspection process refers to the collection of all records or previous appropriate information to better conduct the inspection: Repair report, Tire life sheet, Reason and urgency of inspection request, Operation conditions, Verification of relevant symptoms in the operation among others.

Phase 4. Defining the Type of Inspection:

This phase of the inspection process refers to the scope of the inspection; whether it refers to a partial inspection of a localized area of the tire, or else 100% thereof.

The type of inspection should always be defined because this process allows distributing and managing in an appropriate manner the required time and resources.

Phase 5. Conducting Visual Inspection:

This phase of the inspection process refers to a visual inspection conduction of the area in question, in order to create a particular image of the condition thereof. In this phase the analysts should use the greatest amount of "imaginative" efforts and knowledge of the defect genesis since the progression and guidance of the defects to be detected will be formed thereinafter. This requires relying on quantitative and qualitative judgment elements. In this phase the method of inspection to be used will be defined.

Phase 6. Manual Calculations:

This phase of the inspection process refers to carrying out preliminary basic calculations of the involved thickness, previous to equipment adjustment.

We intend to know the R residual thickness (current) of the tire tread.

Phase 7. Equipment adjustment or calibration:

This "equipment adjustment or calibration" phase refers an accurate adaptation of electronic variables, from which the setting of ultrasonic parameters to carry out measurements is derived.

These parameters are configured for each tire, since the mechanical and acoustic features thereof have been modified due to service in time. In this context, the behavior of acoustic speed with regards to the temperature should be noticed; if the temperature tire is higher than 35° C., the rubber improves its transparency to ultrasound and consequently modifies its speed of sound.

Given the previous explanations we conclude that there are typical referential adjustments or parameters, but in addition there is a group of single parameters for each tire.

Phase 8. Specific ultrasonic readings:

This phase of the inspection process refers to obtaining highly localized readings to rapidly delimit the boundaries of the damaged area so as to subsequently pass to the "Ultrasonic Scanning" stage, which is a continuous scanning without lifting the transducer from the rubber to delimit accurately the defect dimensions and topography thereof.

In this phase the volume or exact area of the defect that affects the tire is obtained in 3D.

Phase 9. Information Analysis:

This phase of the inspection process refers to the analysis of all information collected in the phases for:

a. Obtaining additional information b. Visual inspection c. Specific ultrasonic readings.

After the analysis the technician team is capable of providing a diagnosis of the defect(s) and possible causes thereof.

Phase 10. Diagnosis and Conclusions:

This phase of the inspection process refers to providing the diagnosis of the defect, defect extent, critical state, qualitative and quantitative variable and probable causes related thereof.

Phase 11. Recommendations and Suggestions:

This phase of the inspection process refers to providing a diagnosis and recommendations related to the general tire condition; it involves the study of risk-benefit relation, service restriction, repair feasibility or final disposal.

Phase 12. Technical Report Issuance:

This phase of the Inspection process refers to the issuance of the final inspection report; this report comprises the following information, among others:

Report number and date.

Inspection date and place.

Tire serial or registration number.

Tire model: tire tread design and composition.

Back up digital image of relevant damaged areas.

Digital image of delimited scanning area and number of readings.

Wearing out.

Radial Scheme sectoring tire damaged area.

General remarks.

As to the inspection procedure, we must remember that the ultrasound waves are acoustic waves with different vibration modes, whose frequency ranges between 20 Hz to 20 Kz, above what is perceived by human ear.

The ultrasonic inspection accounts for an interactive dialogue between the analyst, his instrument and the tested tire, a closely connected and inter-independent trilogy that do not admit weakness in any of the parts thereof because it is conceived to provide highly reliable results.

In order to penetrate the tire, the ultrasonic beam must have several physical conditions and features that the ultrasound operator-analyst must adjust in the instrument.

Specifically, if the thickness that the tire must have is known, it is feasible to infer that if the echo travels a smaller distance than expected, then there is an interference that interrupts the ultrasound traveling through the tire. This interference may be the result of any acoustic impedance element of the rubber or a discontinuity in the material, which can be assessed and measured with a high degree of precision and reliability in the diagnosis.

Therefore, according to the above mentioned, it is possible to state that the objective and final purpose of the invention consists in detecting by ultrasound the presence of a defect, reflector or interference inside a OTR tire rubber, with the purpose of assessing the internal condition thereof.

Also it is possible to mention that this technique manages to solve the problem of penetrating rubber thickness greater than 200 mm with ultrasound; changing the old paradigm and fear which supposed that this was not possible.

Rubber, a raw material used in the tire manufacturing, is composed of long polymer chains. The polymer chains are cross-linked by a process called vulcanization to prevent the chains from sliding past each other. The vulcanization process transforms linear chains into a three-dimensional network, binding several chains to each other through knots and the result is known as elastomer.

In the absence of perturbations the chains of an elastomer form the called "statistical coil". If an external force is applied on a rubber sample, such a sample is capable of increasing its size without modifying the valence angles or the binding lengths; it simply presents a more extended conformation. In other words, the tire rubber is formed by long molecules that are capable of stretching or compressing when an external force is applied. The molecule recovers its equilibrium state when this force disappears. Therefore, the process is reversible.

The above-mentioned amorphous structure statistical coil conformation in the rubber cannot vibrate with the ultrasonic senoidal wave due to great ultrasonic energy loss produced by attenuation and dispersion.

Therefore, it is necessary to modify the stimulus or perturbation by introducing a different wave and with a great energetic reserve. To carry this out, the invention uses "square waves", which are produced by alternating current, whose main feature is that it changes rapidly between the maximum and minimum values without passing through intermediate ranges as it occurs with senoidal or triangle waves. Thus, when elastomer chains are impacted by high energy waves, they respond in an organized way to such stimuli and collide with their neighboring chains in and organized way as well until all the energy is dissipated.

As a conclusion it has been established that, in order to detect defects using ultrasound in OTR tires, the ultrasonic defect detector equipment should be, as a general feature, a transmitter of adjustable square waves and a transmitter of impulses with negative or positive peaks, besides transmitting non rectified waves.

The transmitter of adjustable square waves, along with the narrow band filter, achieve an optimal material penetration and signal-noise ratio which position them in the first place for this application.

The signal treatment functions of the equipment should contain a 25 Mhz bandwidth for measurements in thinner places, a transmitter of adjustable square waves to optimize the penetration in thicker or very attenuating areas and narrow bans filters to improve the signal-noise ratio in high-gain applications.

Based on this and as a result of numerous empirical essays, two inspection techniques to be used in tires are deduced: Pulse-Echo and Through-Transmission.

The Pulse-Echo procedure is based on the echo effect that a "reflector" (heterogeneity in the sample core on the surface thereof) produces when it is "illuminated" by an ultrasound beam. In this method the oscillating receptor, either apart or forming a unit with the transmitter (single crystal), receives the "echo" from the reflector and transforms it into the corresponding indication because it operates always through reflection.

Among these methods it is important to differentiate methods that only measure ultrasound traveling time (T), methods which limited to real metrology applications, thickness meters, from methods that measure both parameters (acoustic intensity and traveling time (IT)), which are more versatile for more extended applications in the defectology field, in the material essays. In order to prevent permanent traveling time signals from overlapping and consequently erratic indications in the instrument, it is necessary to resort to the pulse excitation system, thereby the echo-pulse name.

On the other hand, pulse-echo equipments for acoustic intensity and traveling time measurement (IT), as mentioned above, transmit short acoustic pulses at constant intervals so that a periodical response depending on the acoustic pulse travelling time from the oscillating transmitter to the piezoelectric crystal receptor is obtained, as in the case described above. The received acoustic pulse or "echo", coming from the reflection thereof in heterogeneity or in boundary surface of the sample is transformed into a signal or electric pulse which is visualized according to a liquid crystals screen indication whose peak height is proportional to the acoustic pressure reflected by the obstacle.

The Pulse-Echo method for the OTR tire case uses only one scanner or E/R-type transducer (transmitter/receptor) and requires only one contact wall. This straight-beam scanner and longitudinal waves (transverse waves will not do in rubber) introduce square waves in the rubber in the form of packages or pulses at regular intervals with predetermined direction and intensity. The pulses are propagated inside the material until they find an interface that causes a total or partial reflection thereof so that they can be received or captured by the scanner itself. The reflected proportion or smaller energy amplitude (echo) depends mainly on the size and direction of the reflecting surface in relation to the affecting beam energy.

The Through-Transmission method fundamentally differs from the Pulse-Echo technique in this aspect: it uses two transducers which always must be positioned facing each other and very well aligned, with the material to be examined in the middle. One transducer is the transmitter and the other is the receptor (T+R), thereby requiring two accessible contact surfaces which is a significant disadvantage regarding the pulse-echo method, especially when an inspection of a tire assembled to a truck is required. However, its advantage is that because it has only one traveling, the wave gain reserve or "acoustic volume" is higher. Therefore, great energy loss by attenuation is better compensated. The selection of the most appropriate method to be used should be defined according to the ultrasound operator-analyst experience. In any case, the pulse-echo method is the most used method.

In order to interpret the obtained results it is important to know about the defects produced in tires and causes and development thereof to have in situ logical explanations about what the instrument is "telling" us. The ultrasound scanning is equivalent to surfing in an imaginative way through all involved thickness band and through the accidents thereof. The analyst-operator should be able to mentally draw a tri dimensional image of what he is watching in his equipment.

The square wave parameters that have to be adjusted should be saved according to the following: for a material thickness: 150 to 400 mm, preferably, the total thickness of the tire wall to be inspected.

Frequency: 0.10 MHZ to 1.5 MHZ., the range of 0.27 to 1.3 Mhz is preferably used.

Gain: from 40 db to 75 db., a value equivalent to 80% of optimum harmonic value 72.2 dB is preferably used.

Wave propagation speed from 1,200 to 2,500 m/s, the range from 1,810 to 2,200 msec is preferably used.

Wave incident angle: 0.0°

Wave damping from 200 to 400 Ohm, the range from 350 to 400 Ohm is preferably used.

High or low wave filter from 0.1 to 1.5 MHZ, half wave+ 0.3–0.8 Mhz is used when it is rectified, or in Radiofrequency.

Wave power from 100 to 500V, preferably, an optimum value of 400 V.

Once these values are calibrated, an ultrasonic scanning is performed over the tread surface of the desired areas, specially focusing on that areas or stress concentrating points where defects are originated.

In order to obtain a good coupling between the transducer and tire surface, a coupling glycerin with a moisturizing agent with acoustic impedance similar to that of the tested material is used. Low viscosity mineral oils may also be used.

The results obtained are carefully assessed in terms of identifying the causes of the detected defects or damages, assessing its features and magnitude, a qualitative and quantitative approach. In every, inspection, the background document the person in charge is required to provide is the tire record sheet, or "Tire Life" wherein the following data should appear: service hours, No. of truck, Internal Unit No., Serial No., work position, assembly date, removal date and reason, name of the manufacturer, measurements, design or type of tread cross-linkage, etc. Finally, a status diagnostic and prognosis are included, with conclusions and remark with regard to risky operations with restrictions, or normal operation without restrictions.

For every inspected tire an Inspection Technical Report is issued which comprises all relevant information with digital images of the damaged zones en back-up 3D images.

The present invention describes the following relevant and essential advantages among others:

Increased tire unit yield which is translated in working hours.

Rapid and in situ decision taking: sending tire to repair; tire assembly and disassembly.

Real time reliable tire status diagnosis.

3D complete diagnosis of the defect size.

Cost reduction: unnecessary transport expenses.

End of tire destroy and ripping bad practices which occur when workers try to find defects in a blindly way.

End of the need of sending tires to garages to find potential defects.

End of long detection periods wasted in trying to find potential defects by inaccurate and manual traditional methods.

Tire preventive minor repair is facilitated and potentiated.

Spare parts stock availability and control is enhanced, and the assessment of tires that can be repaired is optimized.

It has been demonstrated that by applying ultrasound, defect characteristics can be accurately established and stock availability can be appropriately managed, thereby the end of the tire working period can be predicted more precisely.

A better performance is achieve by assembling non repairable "sick" tires in locations where operations are less stressing or demanding when tires are restricted or in emergency states.

Finally, this specific and particular assessment, by virtue of the developed technical characteristics thereof, is today a Tool for OTR Giant Tire Predictive Symptomatic Service, which allows the early detection of defects, progress follow-up, assessment and repair recommendations in timely manner.

The invention claimed is:

1. Method for inspecting tires having an original thickness, which allows the detection of in situ defects, rubber degradation states, or tire internal condition, wherein said method comprises the following stages:
   a. Calibrating an ultrasonic equipment with specific parameters;
   b. Determining a rubber remaining thickness of the tire and determining wear condition of the tire compared with the original thickness, wherein the tires are off the road tires comprising rims ranging from 22 to 70 inches;
   c. Using said ultrasonic equipment, manually running an ultrasonic scan over the tire wherein the running consists of perfectly conditioned high-energy ultrasonic waves entering into the tire rubber remaining thickness; and
   d. Receiving response echoes from reflections produced by the tire internal defects or discontinuities and collecting information about the internal condition through interpretation of the echoes.

2. Method for inspecting tires according to claim 1, wherein such ultrasound waves are high energy square waves produced by alternating current.

3. Method for inspecting tires according to claim 2, wherein such square waves can be used with its positive, negative peak, or else radiofrequency non-rectified waves.

4. Method for inspecting tires according to claim 1, wherein such ultrasound wave emission and echo reception are performed through the use of a single Transmitter/Receiver type transducer, which interacts through the only contact wall with such tire.

5. Method for inspecting tires according to claim 1, wherein such ultrasound wave emission and reception of responding echoes is performed through the use of transducers which interact with two contact surfaces of such tire, respectively.

6. Method for inspecting tires according to claim 1, wherein such ultrasound waves are square longitudinal-type waves transmitted in the form of packs or pulses at magnitude regular intervals and predetermined direction.

7. Method for inspection tires according to claim 1, wherein the frequency of such waves is between the range of 0.10 to 2.50 MHZ.

8. Method for inspecting tires according to claim 1, wherein the energy reserve gain of such ultrasound waves is within the range from 40 dB to 75 dB.

9. Method for inspecting tires according to claim 1, wherein the propagation speed of such ultrasound waves is within the range of 1,200 to 2,500 m/s.

10. Method for inspecting tires according to claim 1, wherein the incident angle of such ultrasound waves is (0°) zero degrees.

11. Method for inspecting tires according to claim 1 wherein such ultrasound wave damping is within the range of 200-400 Ohm.

12. Method for inspecting tires according to claim 1, wherein such ultrasound wave filter is within the range of 0.1 to 1.5 MHZ.

13. Method for inspecting tires according to claim 1, wherein the power of such ultrasound waves is within the range of 100 to 500 Volts.

14. Method for inspection tires according to claim 1, wherein the frequency of such waves is between 0.5 and 1.8 Mhz.

15. Method for inspecting tires according to claim 1, wherein the energy reserve gain of such ultrasound waves is 72.2 dB.

16. Method for inspecting tires according to claim 1, wherein the propagation speed of such ultrasound waves is within the range of 1,500 to 2,000 m/s.

17. Method for inspecting tires according to claim 1 wherein such ultrasound wave damping is from 350 to 400 Ohm.

18. Method for inspecting tires according to claim 1, wherein such ultrasound wave filter is 0.3 to 0.8 Mhz.

19. Method for inspecting tires according to claim 1, wherein the power of such ultrasound waves is 400 Volts.

* * * * *